(12) United States Patent
Sengun

(10) Patent No.: US 10,383,616 B2
(45) Date of Patent: Aug. 20, 2019

(54) METHODS FOR ATTACHING SOFT TISSUE TO BONE

(71) Applicant: Medos International Sarl, Le Locle (CH)

(72) Inventor: Mehmet Z. Sengun, Canton, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 573 days.

(21) Appl. No.: 15/005,367

(22) Filed: Jan. 25, 2016

(65) Prior Publication Data

US 2017/0209136 A1 Jul. 27, 2017

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0403* (2013.01); *A61B 2017/0412* (2013.01)

(58) Field of Classification Search
CPC ........................... A61B 17/0401; A61B 17/06
USPC ........................... 606/232, 151, 916
See application file for complete search history.

(56) References Cited

U.S. PATENT DOCUMENTS

| | | | |
|---|---|---|---|
| 6,537,319 B2 | 3/2003 | Whelan | |
| 6,949,102 B2 | 9/2005 | Andrews | |
| 8,100,968 B2 | 1/2012 | Chan | |
| 8,114,128 B2 | 2/2012 | Cauldwell et al. | |
| 8,133,257 B2 | 3/2012 | Cook et al. | |
| 8,202,318 B2 | 6/2012 | Willobee | |
| 8,439,976 B2 * | 5/2013 | Albertorio | A61B 17/0401 623/13.14 |
| 8,460,379 B2 * | 6/2013 | Albertorio | A61B 17/0401 623/13.14 |
| 8,591,580 B2 | 11/2013 | Mckernan et al. | |
| 8,821,543 B2 | 9/2014 | Hernandez et al. | |
| 8,882,801 B2 | 11/2014 | DiMatteo et al. | |
| 9,060,763 B2 | 6/2015 | Sengun | |
| 9,179,908 B2 | 11/2015 | Sengun | |
| 9,326,844 B2 * | 5/2016 | Schmieding | A61B 17/0401 |
| 2012/0046746 A1 | 2/2012 | Konicek | |
| 2012/0239145 A1 | 9/2012 | Peterson et al. | |
| 2013/0116730 A1 | 5/2013 | Denham et al. | |

* cited by examiner

*Primary Examiner* — Vy Q Bui

(57) ABSTRACT

Various exemplary methods for attaching soft tissue to bone are provided. In general, a soft tissue can be attached to a bone of a patient using a collapsible suture and a suture anchor. In at least some embodiments, attaching a soft tissue to bone includes use of a suture anchor and a collapsible suture in the form of a collapsible loop. In at least some embodiments, attaching a soft tissue to bone includes use of a suture anchor and a collapsible suture that is cinched with a cinchable knot.

19 Claims, 8 Drawing Sheets

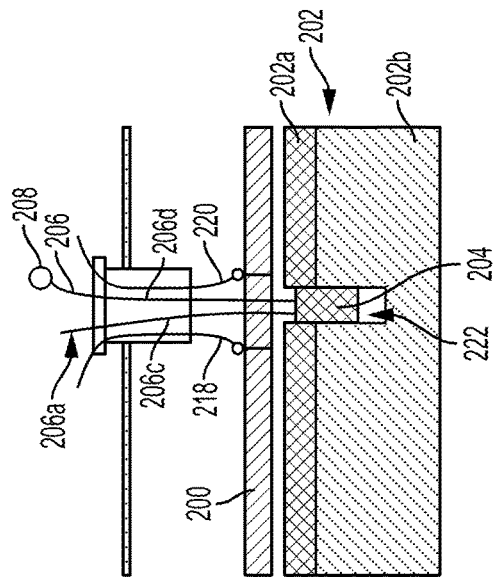
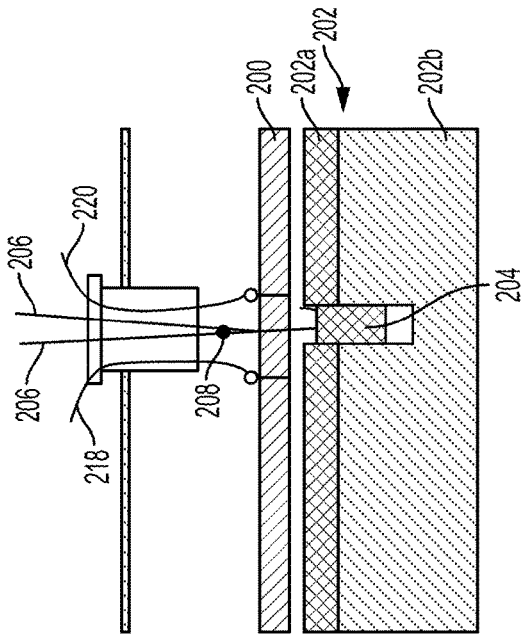
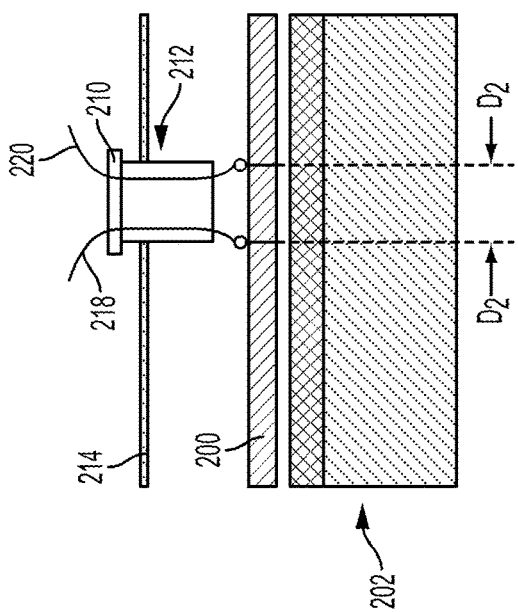
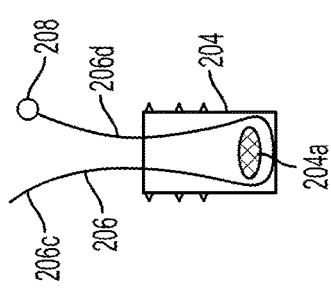
FIG. 16
FIG. 17
FIG. 18
FIG. 19

METHODS FOR ATTACHING SOFT TISSUE TO BONE

FIELD

The present disclosure relates generally to methods for attaching soft tissue to bone.

BACKGROUND

Soft tissues, such as ligaments, tendons, and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures. Some of the more successful methods involve use of a suture anchor to attach a suture to the bone and tying the suture in a manner that holds the tissue in close proximity to the bone. However, sutures tend to rip or slide through soft tissues, such as bicep tendons, that have longitudinally extending fibers. It can therefore be difficult or impossible to repair such soft tissues using suture anchors and sutures.

Accordingly, there remains a need for improved methods for attaching soft tissue to bone.

SUMMARY

In general, methods for attaching soft tissue to bone are provided.

In one aspect, a method for securing soft tissue to bone is provided that in one embodiment includes folding a soft tissue within a body of a patient. The soft tissue is adjacent to a suture anchor disposed in a bone, and the soft tissue has a collapsible suture coupled thereto. The collapsible suture is coupled to the suture anchor. The method also includes securing the folded soft tissue in a folded position with a second suture, and, after securing the folded soft tissue, collapsing the collapsible suture to hold the folded soft tissue in the folded position adjacent to the suture anchor.

The method can vary in any number of ways. For example, the method can include, before folding the soft tissue, trimming an end portion of the soft tissue off the soft tissue to create a trimmed end on a remaining portion of the soft tissue. Folding the soft tissue can include folding the trimmed end of the soft tissue to be next to another portion of the soft tissue.

For another example, the method can include, before folding the soft tissue, partially collapsing the collapsible suture coupled to the soft tissue. Collapsing the collapsible suture after securing the folded tissue can include fully collapsing the collapsible suture.

For yet another example, the second suture can include at least two sutures each having a free end, and securing the folded soft tissue can include tying the free ends together. For still another example, the collapsible suture can include a collapsible loop, and collapsing the collapsible suture can include collapsing the collapsible loop around the folded soft tissue. For another example, collapsing the collapsible suture can include cinching a knot of the collapsible suture. For yet another example, the soft tissue can include a biceps tendon.

In another embodiment, a method for securing soft tissue to bone includes attaching a first suture to a soft tissue of a patient, and with the first suture attached to the soft tissue, folding the soft tissue to form folded layers of the soft tissue. The method also includes securing the folded layers with the first suture such that a collapsible suture is trapped between the folded layers. The collapsible suture is coupled to a suture anchor in bone. The method also includes, after securing the folded layers of the soft tissue, collapsing the collapsible suture.

The method can have any number of variations. For example, the first suture can be attached to the soft tissue, and the soft tissue can be folded with the soft tissue being within a body of the patient. For another example, the soft tissue can be folded in a direction away from the suture anchor in the bone. For yet another example, attaching the first suture to the soft tissue can include wrapping the first suture around the soft tissue or stitching the first suture to the soft tissue. For still another example, the method can include passing the soft tissue through a loop of the collapsible suture before folding the soft tissue, and passing the first suture through the loop before collapsing the collapsible suture. For yet another example, collapsing the collapsible suture can include cinching a knot of the collapsible suture. For another example, the soft tissue can include a biceps tendon.

In another embodiment, a method for securing soft tissue to bone includes attaching first and second sutures to a portion of soft tissue to be attached to or to be reattached to bone. The first and second sutures are spaced apart from one another and each have suture tails extending out of a patient's body. The method also includes inserting a suture anchor into bone. The suture anchor is inserted at a location proximal to an attachment site of the soft tissue. The suture anchor has a collapsible suture extending therefrom and extending out of the patient's body. The method also includes creating a folded segment of the soft tissue, partially collapsing the collapsible suture such that the collapsible suture is within the folded segment adjacent to the suture anchor, attaching the first and second sutures to each other by tying the suture tails together to trap the collapsible suture within the folded segment, and tensioning the collapsible suture to approximate the segment to bone.

The method can vary in any number of ways. For example, the collapsible suture can include a collapsible suture loop, and the method can include passing one of the suture tails through the collapsible loop and passing the segment through the collapsible loop to create a folded segment. For another example, partially collapsing the collapsible suture can include cinching a knot of the collapsible suture. For yet another example, the soft tissue can include a biceps tendon.

In another embodiment, a method for securing soft tissue to bone includes securing a first suture to a soft tissue, and partially collapsing a collapsible suture coupled to a suture anchor in bone adjacent to the soft tissue. The method also includes, after partially collapsing the collapsible suture, folding the soft tissue having the first suture secured thereto. The method also includes securing the folded soft tissue in a folded position by manipulating the first suture, and, after securing the folded soft tissue in the folded position, fully collapsing the collapsible suture to tension the folded soft tissue in relation to the bone.

The method can have any number of variations. For example, the method can include, before folding the soft tissue, passing an end of the soft tissue through a loop of the collapsible suture. Folding the soft tissue can result in a portion of the collapsible suture being located between layers of the folded soft tissue.

For another example, partially collapsing the collapsible suture can result in a portion of the soft tissue extending through a loop of the collapsible suture, and folding the soft tissue can result in a portion of the collapsible suture being located between folded layers of the soft tissue.

For yet another example, the soft tissue can include a biceps tendon.

For still another example, the first suture can include at least two sutures each having a free end. Securing the folded soft tissue can include tying the free ends together.

BRIEF DESCRIPTION OF DRAWINGS

This invention will be more fully understood from the following detailed description taken in conjunction with the accompanying drawings, in which:

FIG. 16 is a side cross-sectional schematic view of another embodiment of first and second sutures tied to a soft tissue above a bone in a body of a patient, the first and second sutures extending through one embodiment of a cannula extending through skin of the patient;

FIG. 17 is a side cross-sectional schematic view of one embodiment of an anchor disposed in a hole in the bone of FIG. 16, the anchor having a third suture coupled thereto that extends through the cannula;

FIG. 18 is a side cross-sectional schematic view of the anchor and the third suture of FIG. 17;

FIG. 19 is a side cross-sectional schematic view of the third suture of FIG. 17 having been partially collapsed;

DETAILED DESCRIPTION

Figure 1:
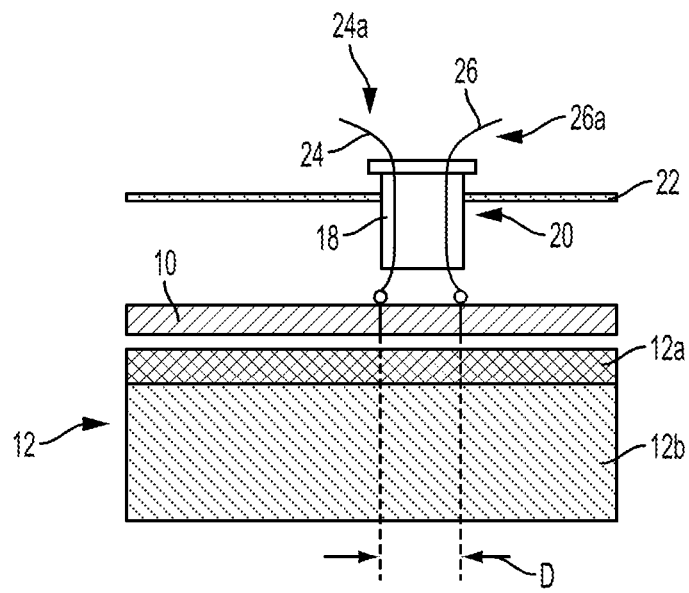
FIG. 1 is a side cross-sectional schematic view of one embodiment of first and second sutures tied to a soft tissue above a bone in a body of a patient, the first and second sutures extending through one embodiment of a cannula extending through skin of the patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods for attaching soft tissue to bone are provided. In general, a soft tissue can be attached to a bone of a patient using a collapsible suture and a suture anchor. The soft tissue can be folded and attached to itself, thereby doubling a load that the soft tissue can carry (as compared to the unfolded soft tissue). The increased carriable load may help hold the tissue in place relative to the bone to facilitate healing and/or may help prevent the suture from ripping through the tissue during performance of the surgical procedure in which the soft tissue is being attached to the bone or during healing after the surgical procedure has been completed.

Traditionally, when a soft tissue is folded as part of a surgical procedure, the soft tissue is pulled out of the patient's body (e.g., pulled out through an incision in skin), folded outside the patient, and then returned into the patient's body (e.g., advanced back into the body through the incision). The incision must therefore be large enough for removal of the unfolded soft tissue therethrough and insertion of the folded soft tissue therethrough such that the surgical procedure ceases to be minimally invasive and accordingly fails to achieve benefits thereof. Folding the tissue outside the patient's body traditionally includes stitching layers of the folded tissue together, which may be time-consuming and/or may involve difficult needle work. The tissue can be folded within the patient's body in the methods described herein, which may facilitate performance of the surgical procedure as a minimally invasive procedure (e.g., an arthroscopic procedure, etc.), which, as will be appreciated by a person skilled in the art, has benefits over non-minimally invasive procedures, such as improved cosmesis and faster healing time. Folding the soft tissue within the patient's body may put less stress on the soft tissue and/or on adjacent body structures since the soft tissue need not be stretched or otherwise maneuvered outside of the patient's body and/or may shorten a length of the surgical procedure since it can take less time to fold the tissue within the patient's body than to remove the tissue and then re-insert the tissue into the patient's body after folding and stitching the tissue outside the patient's body.

Traditionally, in biceps repair, a biceps tendon is put into a bone hole. The size of biceps tendons varies between people, so the bone hole is not a consistent or predictable size between patients and may be a large hole to accommodate large biceps tendons. The bone hole not being a consistent size between patients may make it difficult for a surgeon to determine how large to make a bone hole in a particular patient, may result in a bone hole being formed in the patient that is the wrong size and accordingly require resizing and/or reformation, and/or may make determining the proper size for the bone hole size a time consuming process. The bone hole being large may reduce strength of the bone. Also, biceps repair may not involve use of a suture anchor because the biceps tendon is a relatively weak tendon due to its longitudinal fiber structure. A suture used to connect a suture anchor and a soft tissue having a longitudinal fiber structure, such as a biceps tendon, tends to rip through the soft tissue, thereby leading to prolonged healing, if not complete failure of the tissue repair procedure. Even if the suture is stitched to the soft tissue to help prevent suture tear-out, the stitching traditionally occurs outside the patient's body, which may raise any number of undesirable outcomes, as discussed above. In the methods described herein, a biceps tendon or another type of soft tissue can be attached to a bone using a suture anchor. Bone holes may thus be formed at a consistent and predictable size between patients since the bone hole is sized for the suture anchor, not for the soft tissue, and suture anchors have known, consistent sizes. The soft tissue being folded increases the load that the soft tissue can carry (as compared to the unfolded soft tissue) and hence may reduce chances of the suture used to connect the suture anchor and the soft tissue from ripping through the soft tissue, and/or may allow for the use of very small suture anchors (e.g., anchors 3 mm or even smaller in diameter) since the soft tissue can assume more load bearing responsibilities. Very small suture anchors may provide less patient pain and/or less healing time than larger suture anchors.

Exemplary suture anchors that can be used in the methods described herein include the Healix Advance™ anchor and the Gryphon® suture anchor available from DePuy Mitek of Raynham, Mass., and the suture anchors discussed in U.S. Pat. No. 8,114,128 entitled "Cannulated Suture Anchor" issued Feb. 14, 2012, U.S. Pat. No. 8,882,801 entitled "Dual Thread Cannulated Suture Anchor" issued Nov. 11, 2014, and U.S. Pat. No. 8,133,257 entitled "Bioabsorbable Suture Anchor System For Use In Small Joints" issued Mar. 13, 2012, which are hereby incorporated by reference in their entireties. These suture anchors are examples only, and the methods described herein can be used with other suture anchors.

In an exemplary embodiment, the methods described herein can be used in a biceps repair procedure in which a biceps tendon is attached to bone. The methods described herein can be used in other types of surgical procedures, such as in an Achilles repair, in which an Achilles tendon is attached to bone using a suture anchor, and in other tenodesis procedures in which a tendon is attached to bone using a suture anchor.

In at least some embodiments, attaching a soft tissue to bone includes use of a suture anchor and a collapsible suture in the form of a collapsible loop. In general, the collapsible loop can be attached to the suture anchor and to the soft tissue. The soft tissue can be passed through the collapsible loop, the soft tissue can then be folded, and the collapsible loop can be then collapsed around the folded tissue to secure the soft tissue to the bone via the suture anchor.

FIGS. 1, 2, and 4-8 illustrate one embodiment of a method of attaching a soft tissue 10 to a bone 12 of a patient using a suture anchor 14 and a collapsible suture 16 including a collapsible loop 16a. The anchor 14 and the collapsible suture 16 are also illustrated in FIG. 3 with the suture 16 extending around a suture-engaging member 14a in a distal portion of the anchor 14.

As shown in FIG. 1, the soft tissue 10 and the bone 12 within the patient's body are accessed through a cannula 18 positioned within an opening 20 formed in skin 22 of the patient. The cannula 18 generally provides a passageway from outside the patient's body to inside the patient's body through an inner passageway extending therethrough. As will be appreciated by a person skilled in the art, the cannula 18 can have any of a variety of configurations. As will also be appreciated by a person skilled in the art, the cannula 18 can be positioned in the opening 20 in the skin 22 in any of a variety of ways. For example, the opening 20 can be formed in the skin 22 using a cutting instrument (e.g., a scalpel, etc.), and the cannula 18 can be advanced into the opening 20 such that a proximal portion of the cannula 18 is positioned external to the skin 22 and a distal portion of the cannula 18 is positioned underneath the skin 22. Such positioning of the cannula 18 is shown in FIGS. 1, 2, and 4-8. For another example, the cannula 18 can be advanced through the skin 22 without the opening 20 being preformed. The cannula 18 can have a sharp distal end that forms the opening 20 as the cannula 18 is advanced through the skin 22. The cannula 18 can be advanced through the skin 22 until the proximal portion of the cannula 18 is positioned external to the skin 22 and the distal portion of the cannula 18 is positioned underneath the skin 22.

Although the soft tissue 10 and the bone 12 are accessed through a cannula 18 in this illustrated embodiment, the soft tissue 10 and the bone 12 within the patient's body can be accessed in any of a variety of other ways, as will be appreciated by a person skilled in the art, such as by being accessed directly through the skin 22 without use of a cannula or other type of access device.

As also shown in FIG. 1, a first suture 24 and a second suture 26 are each attached to the tissue 10. The first and second suture 24, 26 can be attached to the tissue 10 in any order, e.g., the first suture 24 before the second suture 26 or the second suture 26 before the first suture 24. The first and second sutures 24, 26 are attached to the tissue 10 with the tissue 10 being in the body of the patient, thereby helping to preserve the minimally invasive nature of the surgical procedure.

The first suture 24 attached to the tissue 10 extends out of the patient's body, e.g., out through the cannula 18, with a tail or free end 24a of the first suture 24 located outside of the patient's body. Similarly, the second suture 26 attached to the tissue 10 extends out of the patient's body, e.g., out through the cannula 18, with a tail or free end 26a of the second suture 26 located outside of the patient's body.

The first suture 24 is attached to the tissue 10 at a first location along a longitudinal length of the tissue, and the second suture 26 is attached to the tissue 10 at a second location along the tissue's longitudinal length that is spaced a distance D away from the first location along the tissue's longitudinal length. Having the first and second locations spaced apart by the distance D provides space between the first and second sutures 24, 26 along the tissue's longitudinal length. The collapsible loop 16 can be collapsed around the tissue 10 within this space, as discussed further below. The distance D is large enough to allow enough space for the collapsible suture 16 and for the tissue 10 to be folded between the first and second locations, as also discussed further below. In an exemplary embodiment, the distance D is about 20 mm, but the distance D can be smaller or larger depending on one or more factors, e.g., diameter of the anchor 14, thickness of the tissue 10, etc.

The first and second sutures 24, 26 are attached to the tissue 10 by being tied therearound in this illustrated embodiment, but the first and second suture 24, 26 can be attached to the tissue 10 in other ways. Examples of suture tying techniques are described in U.S. Pat. No. 9,060,763 entitled "Systems, Devices, And Methods For Securing Tissue" issued Jun. 23, 2015, which is hereby incorporated by reference, although other suture tying techniques can be used to tie the first and second sutures 24, 26 to the tissue 10. The tied first and second sutures 24, 26 can each be secured with multiple knots for increased security over a single knot, as will be appreciated by a person skilled in the art.

The first suture 24, the second suture 26, and the collapsible suture 16 each include a single suture strand in this illustrated embodiment, but any one or more of the first suture 24, the second suture 26, and the collapsible suture 16 can include a plurality suture strands, which may help ensure that healing can still occur if any of the suture strands in the plurality of suture strands fails (e.g., breaks, tears through tissue, etc.) since at least one other suture strand can still be effective.

Figure 2:
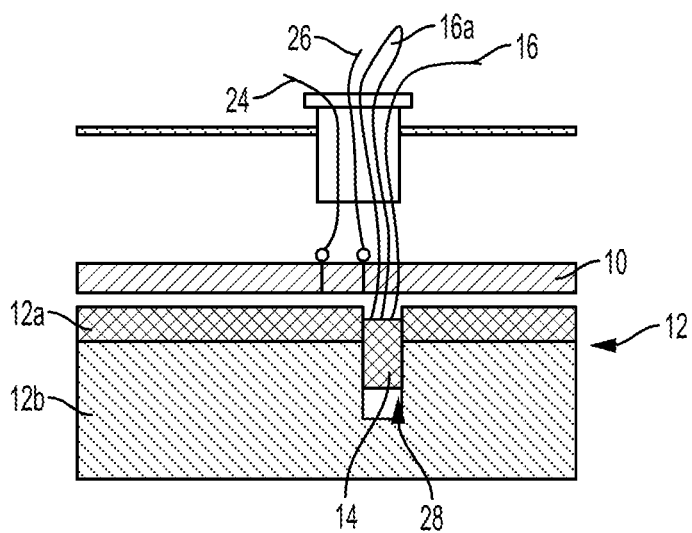
FIG. 2 is a side cross-sectional schematic view of one embodiment of an anchor disposed in a hole in the bone of FIG. 1, the anchor having a third suture coupled thereto that extends through the cannula.
Figure 3:
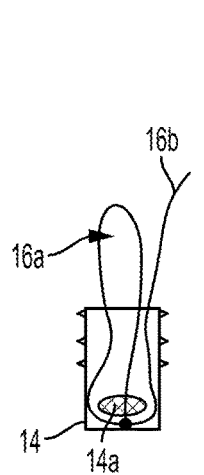
FIG. 3 is a side cross-sectional schematic view of the anchor and the third suture of FIG. 2.

As shown in FIG. 2, the suture anchor 14 is disposed in a hole 28 in the bone 12 adjacent to the soft tissue 10. As will be appreciated by a person skilled in the art, the anchor 14 can be disposed in the hole 28 in any of a variety of ways, such as by using a disposal technique discussed in previously mentioned U.S. Pat. No. 8,114,128 entitled "Cannulated Suture Anchor" issued Feb. 14, 2012, U.S. Pat. No. 8,882,801 entitled "Dual Thread Cannulated Suture Anchor" issued Nov. 11, 2014, and U.S. Pat. No. 8,133,257 entitled "Bioabsorbable Suture Anchor System For Use In Small Joints" issued Mar. 13, 2012. The anchor 14 is disposed in the bone 12 with a proximal portion thereof in cortical bone 12a of the bone 12 and a distal portion thereof in cancellous bone 12b of the bone 12 that underlies the cortical bone 12a. In other embodiments, the anchor 14 can be disposed within entirely one or the other of the cortical and cancellous bone 12a, 12b.

The collapsible suture 16 is coupled to the anchor 14. As also shown in FIG. 2, the collapsible suture 16 extends out of the patient's body, e.g. out through the cannula 18, with the collapsible loop 16a of the collapsible suture 16 and a tail or free end 16b of the collapsible suture 16 located outside of the patient's body. In an exemplary embodiment, the collapsible suture 16 is coupled to the anchor 14, e.g., as shown in FIG. 3, before the anchor 14 is disposed in the bone 12. The collapsible suture 16 being coupled to the anchor 14 before the anchor 14 is disposed in the bone 12 may facilitate proper positioning of the collapsible suture 16 with the collapsible loop 16a and tail 16b being accessible external to the patient's body. In at least some embodiments, the collapsible suture 16 can be pre-loaded in the anchor 14, e.g., as shown in FIG. 3, before the anchor 14 is advanced into the patient's body, such as by being pre-loaded during manufacturing or by being pre-loaded by the surgeon or other medical personnel as part of surgery preparation. Exemplary couplings of a collapsible loop and a suture anchor are discussed in U.S. Pat. No. 8,821,543 entitled "Adjustable Anchor Systems And Methods" issued Sep. 2, 2014, which is hereby incorporated by reference in its entirety, although other types of couplings can be used.

The first suture 24, second suture 26, and collapsible suture 16 can be uniquely identifiable from one another to facilitate selection and manipulation of intended one(s) of the sutures 24, 26, 16 quickly and without guessing. The first suture 24, second suture 26, and collapsible suture 16 can be uniquely identifiable in any of a variety of ways, such as by being different colors, by having different sizes (e.g., different diameters), and/or by having different thread patterns.

In an exemplary embodiment, the anchor 14 is disposed in the bone 12 after the first and second sutures 24, 26 have been attached to the tissue 10, which may help ensure that the anchor 14 is positioned to one side (the right side in the view of FIG. 2) of the first and second locations where the tissue 10 is attached to the first and second sutures 24, 26. Such positioning of the anchor 14 may facilitate positioning of the tail 16b and the loop 16a of the collapsible suture 16 that is coupled to the anchor 14 to one side of the tails 24a, 26a of the first and second sutures 24, 26 outside the patient's body, as shown in FIG. 2, which may help prevent suture tangling and/or may facilitate passage of one of the first and second sutures' tails 24a, 26b through the collapsible loop 16a outside the patient's body.

Figure 4:
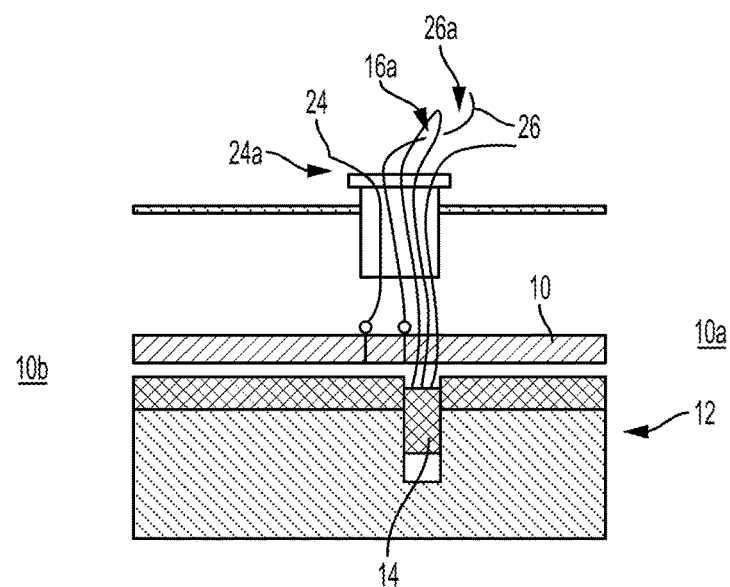
FIG. 4 is a side cross-sectional schematic view of a free end of the second suture passed through a collapsible loop of the third suture of FIG. 2.
Figure 5:
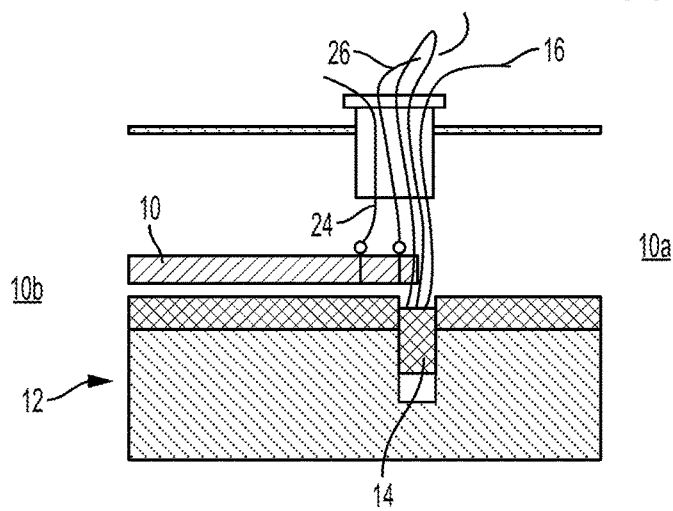
FIG. 5 is a side cross-sectional schematic view of the soft tissue of FIG. 4 with one end thereof having been removed.

As illustrated in FIG. 4, one of the first and second sutures' tails 24a, 26b is passed through the collapsible loop 16a outside the patient's body. The one of the first and second sutures' tails 24a, 26b selected for this passage is the one of the tails 24a, 24b that is closer to the end of the tissue 10 that will be (or is already) trimmed. That one of the first and second sutures 24, 26 in this illustrated embodiment is the second suture 26, which is closer to one side 10a of the tissue 10 that will be trimmed. FIG. 5 shows the end of the tissue 10 trimmed on that side 10a of the tissue 10 after the end of the one of the first and second sutures' tails 24a, 26b (the second suture's tail 26a) has been passed through the collapsible loop 16a. The tissue 10 can, however, be trimmed at any time during the surgical procedure prior to the one of the first and second sutures' tails 24a, 26b being passed through the collapsible loop 16a. The tissue 10 can be trimmed in any of a variety of ways, as will be appreciated by a person skilled in the art. The other side 10b of the tissue 10 remains untrimmed, e.g., remains attached to a body structure such as muscle. The trimming of the tissue 10 facilitates folding of the tissue 10, as discussed further below, by detaching an end of the tissue 10 from the bone 12.

Figure 6:
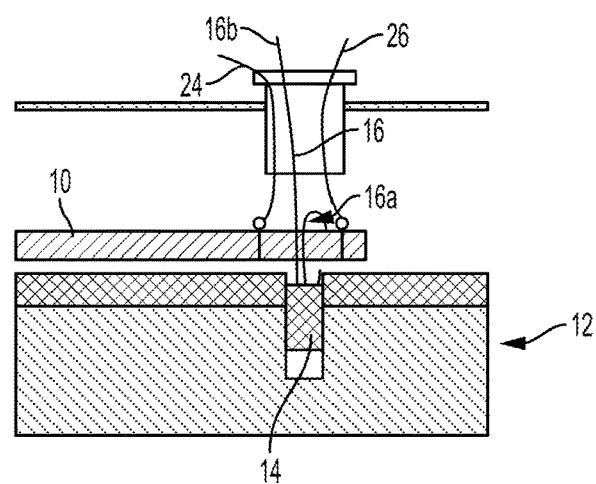
FIG. 6 is a side cross-sectional schematic view of the third suture of FIG. 5 having been partially collapsed.
Figure 7:
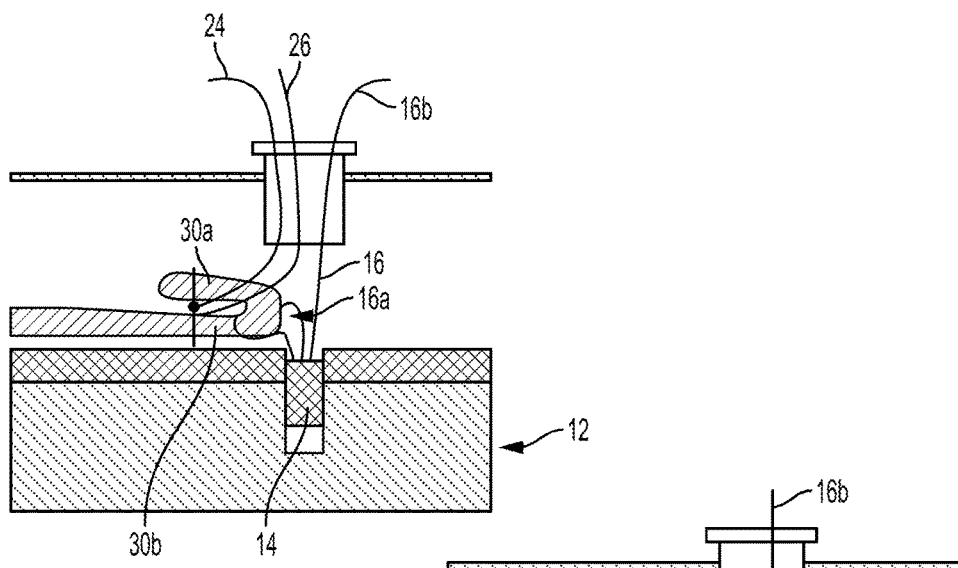
FIG. 7 is a side cross-sectional schematic view of the soft tissue and the first and second sutures of FIG. 6 with the soft tissue having been folded and the first and second sutures having been tied together.

The trimmed end of the tissue 10 is passed through the collapsible loop 16a within the body of the patient. The collapsible loop 16a is then partially collapsed, as shown in FIG. 6, to position the collapsible loop 16a between the first and second sutures 24, 26 within the space therebetween. The tissue 10 is then folded, as shown in FIG. 7, with the trimmed end of the tissue 10 being folded toward the other end of the tissue 10, thereby forming two layers 30a, 30b of folded tissue 10 with the collapsible suture 16, e.g., the collapsible loop 16a, positioned therebetween. The tissue 10 is folded such that the first and second locations, where the first and second sutures 24, 26 are attached to the tissue 10, are aligned. Thus, a midpoint between the first and second locations (e.g., D÷2) can define a fold point of the tissue 10. The distance D between the first and second locations where the first and second sutures 24, 26 are attached to the tissue 10 can thus define a length of each of the layers 30a, 30b, with each of the layers 30a, 30b having a length of about half the distance D.

As shown in FIG. 7, with the tissue 10 folded, the first and second sutures 24, 26 are tied together, e.g., the tails 24a, 26a of the first and second sutures 24, 26 are tied together, to secure the tissue 10 in a folded position, e.g., to secure the layers 30a, 30b together. Securing the tissue 10 in the folded position traps the collapsible suture 16, e.g., the collapsible loop 16b between the layers 30a, 30b. The collapsible loop 16a only being partially collapsed, e.g., not being fully collapsed, when the first and second sutures 24, 26 are tied together may help the collapsible loop 16a move to be positioned at an apex of the fold (if not already so positioned pre-fold), e.g., adjacent the fold point, and/or may help make it easier to secure the layers 30a, 30b of the tissue 10 since the collapsible suture 16 will have slack and accordingly will not be exerting a force upon the tissue 10 that could make the tying difficult.

Figure 8:
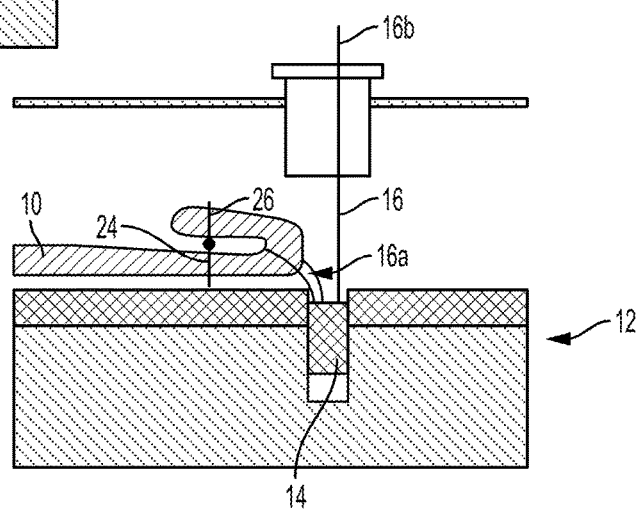
FIG. 8 is a side cross-sectional schematic view of the first, second, and third sutures of FIG. 7 with the third suture having been fully collapsed and the first and second sutures having been trimmed.
Figure 9:
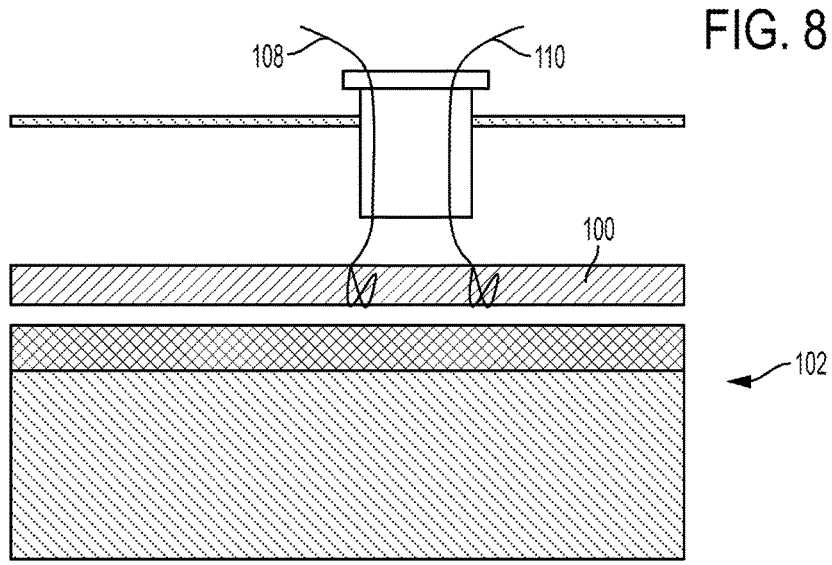
FIG. 9 is a side cross-sectional schematic view of another embodiment of first and second sutures stitched to a soft tissue above a bone in a body of a patient, the first and second sutures extending through one embodiment of a cannula extending through skin of the patient.
Figure 10:
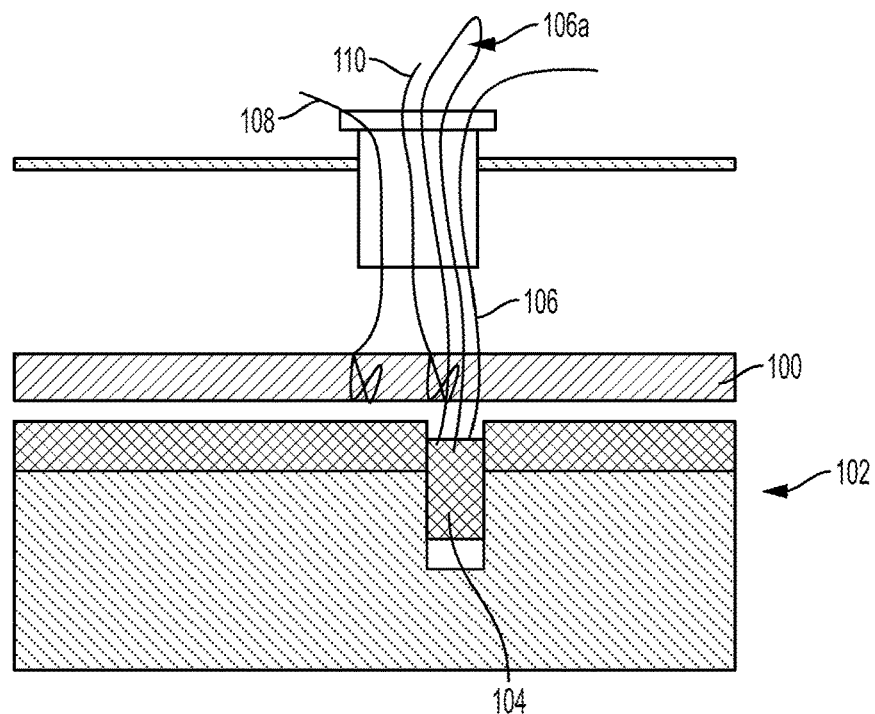
FIG. 10 is a side cross-sectional schematic view of one embodiment of an anchor disposed in a hole in the bone of FIG. 9, the anchor having a third suture coupled thereto that extends through the cannula.
Figure 11:
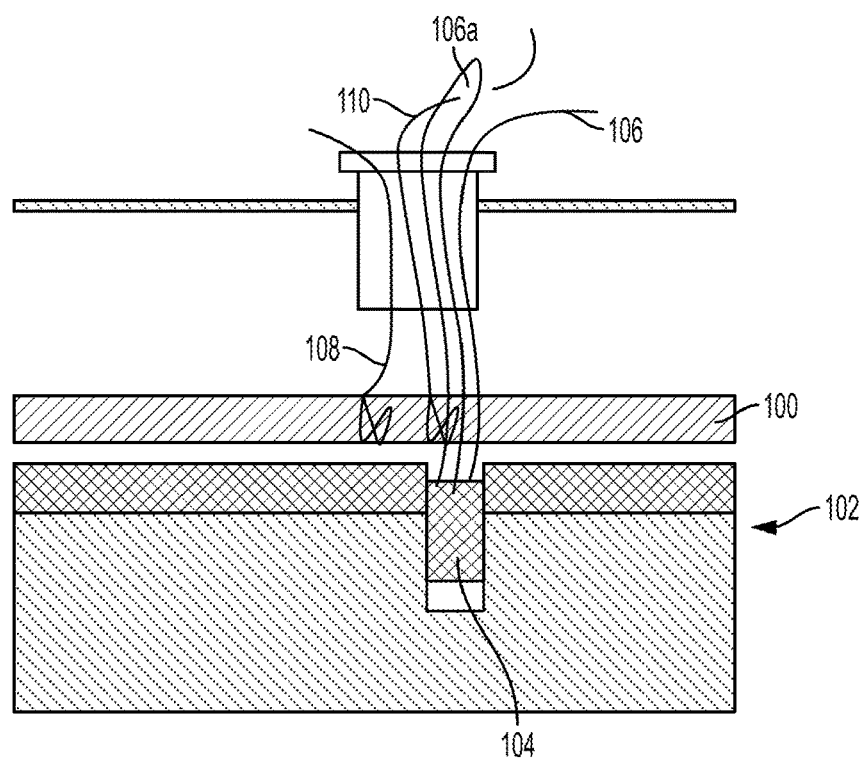
FIG. 11 is a side cross-sectional schematic view of a free end of the second suture passed through a collapsible loop of the third suture of FIG. 10.
Figure 12:
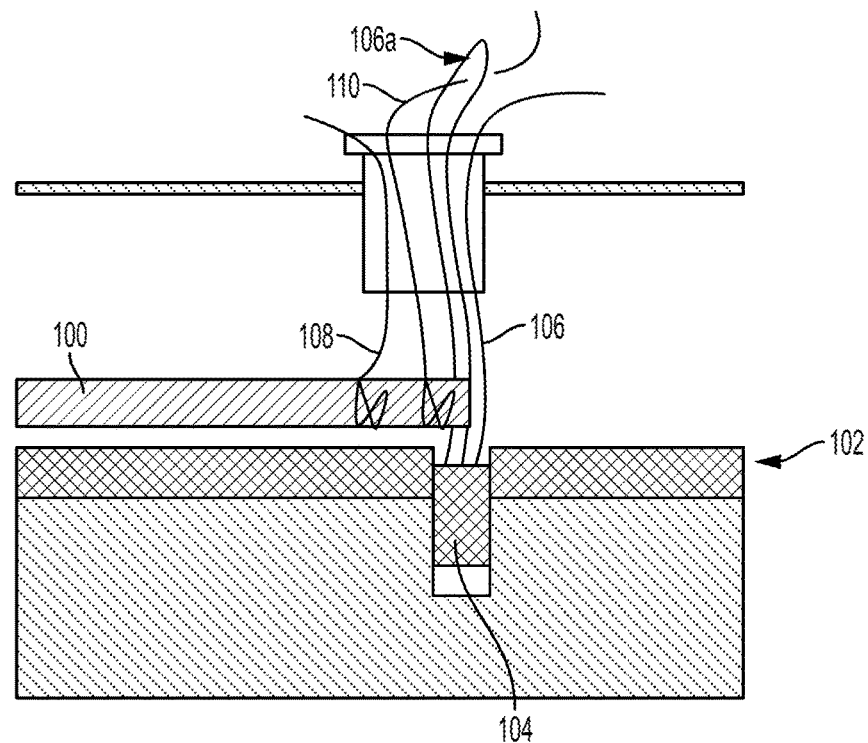
FIG. 12 is a side cross-sectional schematic view of the soft tissue of FIG. 11 with one end thereof having been removed.
Figure 13:
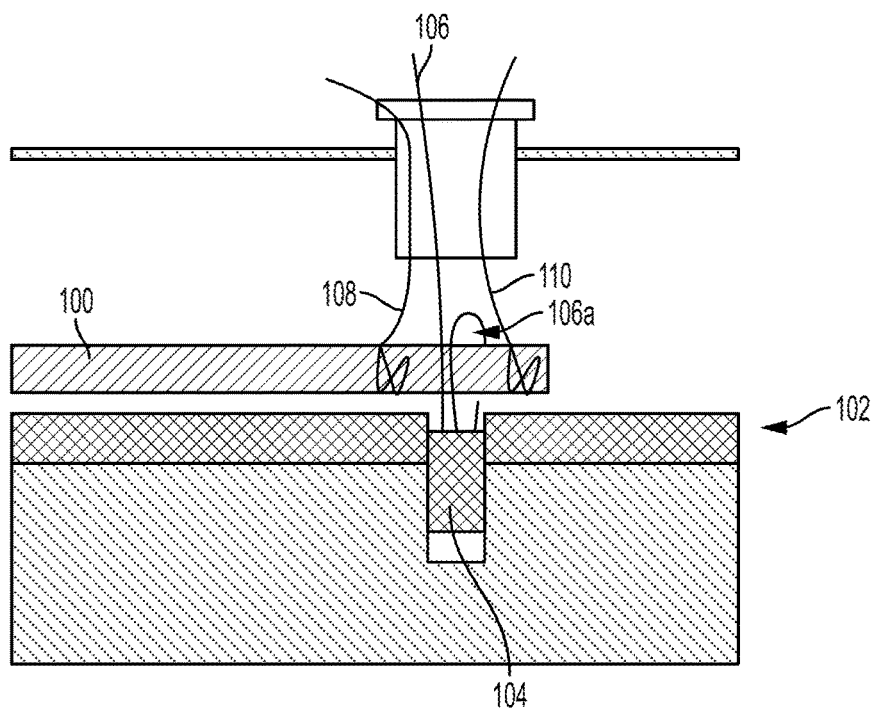
FIG. 13 is a side cross-sectional schematic view of the third suture of FIG. 12 having been partially collapsed.
Figure 14:
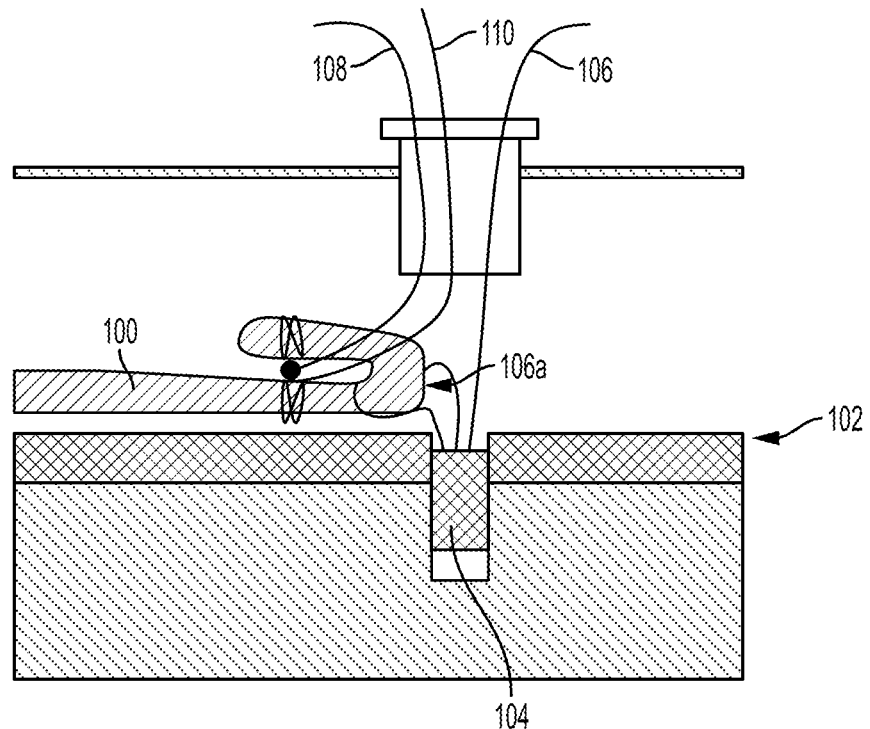
FIG. 14 is a side cross-sectional schematic view of the soft tissue and the first and second sutures of FIG. 13 with the soft tissue having been folded and the first and second sutures having been tied together.
Figure 15:
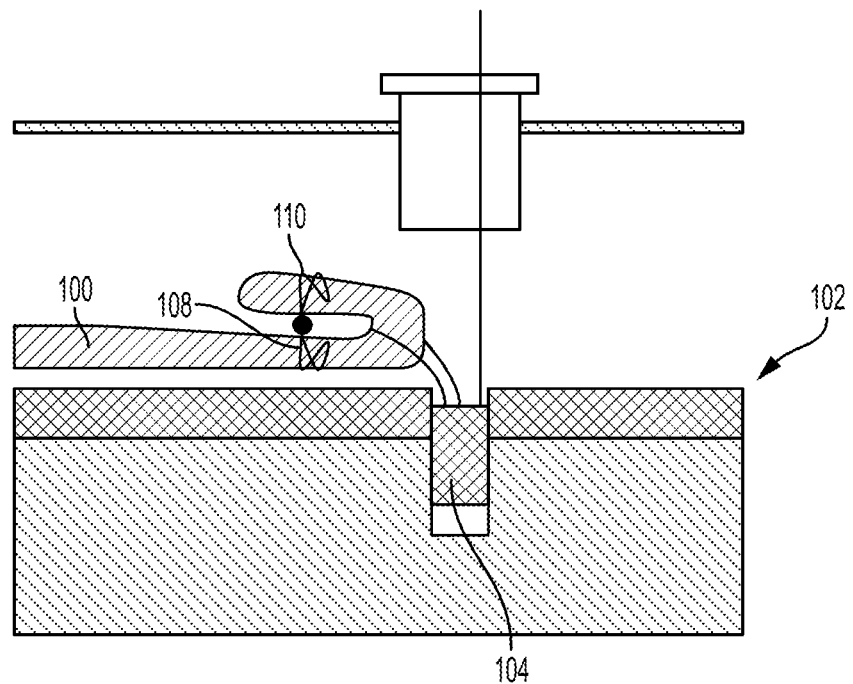
FIG. 15 is a side cross-sectional schematic view of the first, second, and third sutures of FIG. 14 with the third suture having been fully collapsed and the first and second sutures having been trimmed.

As shown in FIG. 8, with the tissue 10 secured in the folded position, e.g., after tying the first and second sutures 24, 26 together, the collapsible suture 16 is tensioned, e.g., by pulling on the collapsible suture's tail 16b outside the patient's body, to fully collapse the collapsible loop 16a. The tissue 10 is thereby pulled into closer and/or tighter contact with a surface of the bone 12, e.g., with a surface of the cortical bone 12a, which may facilitate healing. The collapsible suture 16 extends width-wise across the tissue 10, e.g., transverse to a longitudinal axis of the tissue 10. The collapsible suture 16 may thus be less likely to tear through the tissue 10 when the tissue 10 has longitudinal fibers because the collapsible suture 16 extends transversely to the longitudinal fibers.

With the collapsible suture 16 fully collapsed, the collapsible suture 16 can be trimmed to a desired length so as to no longer extend out of the patient's body, and the cannula 18 can be removed from the opening 20 within the skin 22.

FIGS. 9-15 illustrate another embodiment of a method of attaching a soft tissue 100 to a bone 102 using a suture anchor 104 and a collapsible suture 106 including a collapsible loop 106a. The stages of the method illustrated in FIGS. 9-15 correspond to the stages of the method illustrated in FIGS. 1, 2, and 4-8, respectively. In the embodiment of FIGS. 9-15, however, first and second sutures 108, 110 are attached to the tissue 100 by being stitched thereto instead of being tied to tissue like the first and second sutures 24, 26 of the embodiment of FIGS. 1, 2, and 4-8 that are tied to the tissue 10.

In at least some embodiments, attaching a soft tissue to bone includes use of a suture anchor and a collapsible suture that is cinched with a cinchable knot. In general, the collapsible suture can include a cinchable knot and can be attached to the suture anchor and to the soft tissue. The soft tissue can be folded with the collapsible suture attached thereto, and the cinchable knot can be then cinched to secure the folded soft tissue to the bone via the suture anchor. Exemplary collapsible sutures cinchable with a knot are discussed in U.S. Pat. No. 9,179,908 entitled "Surgical Filament Snare Assemblies" issued Nov. 10, 2015, which is hereby incorporated by reference in its entirety, and in previously mentioned U.S. Pat. No. 9,060,763 entitled "Systems, Devices, And Methods For Securing Tissue" issued Jun. 23, 2015 and U.S. Pat. No. 8,821,543 entitled "Adjustable Anchor Systems And Methods" issued Sep. 2, 2014, although other types of collapsible sutures cinchable with a knot may be used. The collapsible sutures cinchable with a knot that may be attached to a fixed length loop in performing some surgical procedures need not include the fixed length loop attached thereto when used in the methods described herein.

FIGS. 16, 17, and 19-22 illustrate one embodiment of a method of attaching a soft tissue 200 to a bone 202 using a suture anchor 204 and a collapsible suture 206 that is cinched with a cinchable knot 208. The anchor 204 and the collapsible suture 206 are also illustrated in FIG. 18 with the suture 206 extending around a suture-engaging member 204a in a distal portion of the anchor 204.

As shown in FIG. 16, the soft tissue 200 and the bone 202 within the patient's body are accessed through a cannula 210 positioned within an opening 212 formed in skin 214 of the patient similar to that discussed above regarding the cannula 10 of the embodiment of FIG. 1. Also similar to that discussed above with respect to the embodiment of FIG. 1, access to the patient's body can be achieved using the cannula 210 or in another way.

As also shown in FIG. 16, a first suture 218 and a second suture 220 are each attached to the tissue 200 by being tied thereto spaced a distance D2 apart from one another, similar to that discussed above regarding the first and second sutures 24, 26 of the embodiment of FIG. 1 being tied to the tissue 10 at the distance D apart from one another. The first and second sutures 218, 220 can be attached to the tissue 200 in other ways, such as by stitching, as discussed above. The first and second sutures 218, 220 are attached to the tissue 200 with the tissue 200 being in the body of the patient, thereby helping to preserve the minimally invasive nature of the surgical procedure. The first suture 218, second suture 220, and collapsible suture 206 can be uniquely identifiable from one another in any of a variety of ways, as discussed above, and each of the first suture 218, second suture 220, and collapsible suture 206 can include one or more suture strands, as also discussed above.

As shown in FIG. 17, the suture anchor 204 is disposed in a hole 222 in the bone 202 adjacent to the soft tissue 200, similar to that discussed above regarding the anchor 14 being disposed in the bone 12. The anchor 204 has a proximal portion thereof in cortical bone 202a of the bone 202 and a distal portion thereof in cancellous bone 202b of the bone 202 that underlies the cortical bone 202a, but as also discussed above, the anchor 204 can be otherwise positioned in the bone 202.

The collapsible suture 206 is coupled to the anchor 204. As also shown in FIG. 17, the collapsible suture 206 extends out of the patient's body, e.g. out through the cannula 210, with the cinchable knot 208 of the collapsible suture 206 and a tail or free end 206a of the collapsible suture 206 located outside of the patient's body. In an exemplary embodiment, the collapsible suture 206 is coupled to the anchor 204, e.g., as shown in FIG. 18, before the anchor 204 is disposed in the bone 202. The collapsible suture 206 being coupled to the anchor 204 before the anchor 204 is disposed in the bone 202 may facilitate proper positioning of the collapsible suture 206 with the tail 206a and knot 208 external to the patient's body and limbs 206c, 206d of the suture 206 to be on opposite sides of the tissue 200 as illustrated in FIG. 17. In at least some embodiments, the collapsible suture 206 can be pre-loaded in the anchor 204, e.g., as shown in FIG. 18, before the anchor 204 is advanced into the patient's body, such as by being pre-loaded during manufacturing or by being pre-loaded by the surgeon or other medical personnel as part of surgery preparation.

In an exemplary embodiment, the anchor 204 is disposed in the bone 202 after the first and second sutures 218, 220 have been attached to the tissue 200 to help ensure that the anchor 204 is positioned between the first and second locations where the tissue 200 is attached to the first and second sutures 218, 220, e.g., the anchor 204 being within the length of tissue 200 defined by the distance D2. Such positioning may facilitate positioning of the collapsible suture 206 between layers of the tissue 200 before the tissue 200 has been folded, as discussed further below.

Figure 20:
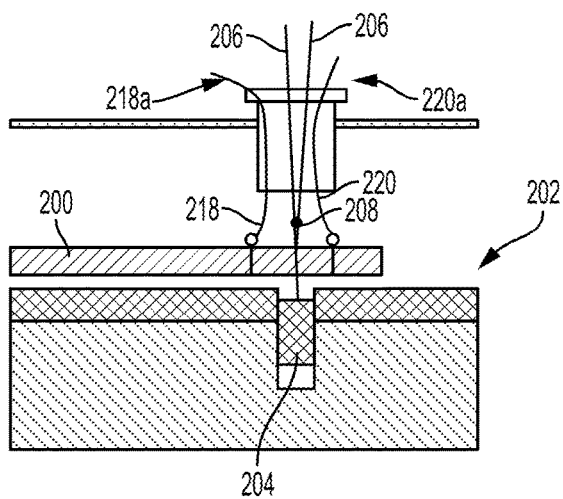
FIG. 20 is a side cross-sectional schematic view of the soft tissue of FIG. 19 with one end thereof having been removed.

With the first and second sutures 218, 220 attached to the tissue 200 and the limbs 206c, 206d of the collapsible suture 206 passed around the tissue 200, the collapsible suture 206 is partially collapsed, as shown in FIG. 19, and one end of the tissue 200 is trimmed, as shown in FIG. 20. The trimming of the tissue 200 and the partial collapsing of the suture 206 can occur in any order, e.g., the trimming before the partial collapsing or the trimming after the partial collapsing. The tissue 200 can be trimmed in any of a variety of ways, as will be appreciated by a person skilled in the art. The other side of the tissue 200 remains untrimmed, e.g., remains attached to a body structure such as muscle. The trimming of the tissue 200 facilitates the folding of the tissue 200. The partial collapse of the collapsible suture 206 moves the knot 208 from outside the patient's body to within the patient's body to position the knot 208 near the tissue 200.

Figure 21:
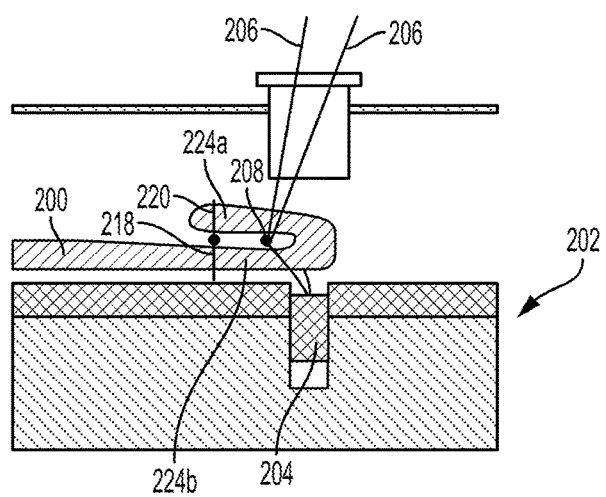
FIG. 21 is a side cross-sectional schematic view of the soft tissue and the first and second sutures of FIG. 20 with the soft tissue having been folded and the first and second sutures having been tied together and trimmed.

With the tissue 200 trimmed and the collapsible suture 206 partially collapsed, the tissue 200 is folded, as shown in FIG. 21, thereby forming two layers 224a, 224b of folded tissue 200 with the collapsible suture 206 and the knot 208 thereof positioned therebetween. The side of the tissue 200 that is trimmed is the side that is folded toward the anchor 204 and toward the other end of the tissue 200. The tissue 200 is folded such that the first and second locations, where the first and second sutures 218, 220 are attached to the tissue 200, are aligned. Thus, a midpoint between the first and second locations (e.g., D2÷2) can define a fold point of the tissue 200. The distance D2 between the first and second locations where the first and second sutures 218, 220 are attached to the tissue 200 can thus define a length of each of the layers 224a, 224b, with each of the layers 224a, 224b having a length of about half the distance D2. The collapsible suture 206 can be positioned around the tissue 200 with the limbs 206c, 206d on either side thereof, as shown in FIG. 17, at the midpoint (as measured during the surgical procedure or as best estimated by a surgeon or other medical personnel who is positioning the collapsible suture 206 relative to the tissue 200), which may help ensure that the knot 208 is positioned between the layers 224a, 224b of the folded tissue 200.

As shown in FIG. 21, with the tissue 200 folded, the first and second sutures 218, 220 are tied together, e.g., tails 218a, 220a of the first and second sutures 218, 220 are tied together, to secure the tissue 200 in a folded position, e.g., to secure the layers 224a, 224b together. Securing the tissue 200 in the folded position traps the collapsible suture 206, including the cinchable knot 208 thereof, between the layers 224a, 224b. The collapsible suture 206 only being partially collapsed, e.g., not being fully collapsed, when the first and second sutures 218, 220 are tied together may help the knot 208 be positioned at an apex of the fold (if not already so positioned pre-fold) and/or may help make it easier to secure the layers 224a, 224b of the tissue 200 since the collapsible suture 206 will have slack and accordingly will not be exerting a force upon the tissue 200 that could make the tying difficult.

Figure 22:
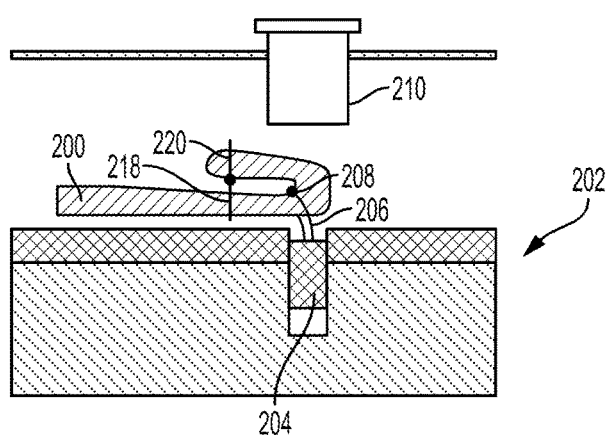
FIG. 22 is a side cross-sectional schematic view of the third suture of FIG. 21 with the third suture having been fully collapsed and trimmed.

As shown in FIG. 22, with the tissue 200 secured in the folded position, e.g., after tying the first and second sutures 218, 220 together, the collapsible suture 206 is tensioned, e.g., by pulling on the collapsible suture 206 outside the patient's body, to fully collapse the collapsible suture 206 and fully tighten the knot 208. The tissue 200 is thereby pulled into closer and/or tighter contact with a surface of the bone 202, e.g., with a surface of the cortical bone 202a, which may facilitate healing. Additional half hitches may be added, if desired by the surgeon or other user. The collapsible suture 206 extends width-wise across the tissue 200, e.g., transverse to a longitudinal axis of the tissue 200. The collapsible suture 206 may thus be less likely to tear through the tissue 200 when the tissue 200 has longitudinal fibers because the collapsible suture 206 extends transversely to the longitudinal fibers.

With the collapsible suture 206 fully collapsed, the collapsible suture 206 can be trimmed to a desired length so as to no longer extend out of the patient's body, and the cannula 210 can be removed from the opening 212 within the skin 214.

A person skilled in the art will appreciate that the implementations described herein have application in conventional minimally-invasive and open surgical instrumentation as well application in robotic-assisted surgery.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for securing soft tissue to bone, comprising:
folding a soft tissue within a body of a patient, the soft tissue being adjacent to a suture anchor disposed in a bone, and the soft tissue having a collapsible suture coupled thereto, the collapsible suture being coupled to the suture anchor;

securing the folded soft tissue in a folded position with a second suture, wherein the second suture includes at least two sutures; and after securing the folded soft tissue, collapsing the collapsible suture to hold the folded soft tissue in the folded position adjacent to the suture anchor.

2. The method of claim 1, further comprising, before folding the soft tissue, trimming an end portion of the soft tissue off the soft tissue to create a trimmed end on a remaining portion of the soft tissue.

3. The method of claim 2, wherein folding the soft tissue includes folding the trimmed end of the soft tissue to be next to another portion of the soft tissue.

4. The method of claim 1, wherein the collapsible suture is located between folded layers of the folded soft tissue.

5. The method of claim 1, further comprising, before folding the soft tissue, partially collapsing the collapsible suture coupled to the soft tissue;
wherein collapsing the collapsible suture after securing the folded tissue includes fully collapsing the collapsible suture.

6. The method of claim 1, wherein the at least two sutures each has a free end, and securing the folded soft tissue includes tying the free ends together.

7. The method of claim 1, wherein the collapsible suture includes a collapsible loop, and collapsing the collapsible suture includes collapsing the collapsible loop around the folded soft tissue.

8. The method of claim 1, wherein collapsing the collapsible suture includes cinching a knot of the collapsible suture.

9. The method of claim 1, wherein the soft tissue includes a biceps tendon.

10. A method for securing soft tissue to bone, comprising:
attaching a first suture and a second suture to a soft tissue of a patient;
passing the soft tissue through a loop of a collapsible suture;
passing the first suture through the loop;
with the first and second sutures attached to the soft tissue and after passing the soft tissue through the loop, folding the soft tissue to form folded layers of the soft tissue;
securing the folded layers with the first and second sutures such that the collapsible suture is trapped between the folded layers, the collapsible suture being coupled to a suture anchor in bone; and
after securing the folded layers of the soft tissue and after passing the first suture through the loop, collapsing the collapsible suture.

11. The method of claim 10, wherein the first and second sutures are attached to the soft tissue, and the soft tissue is folded with the soft tissue being within a body of the patient.

12. The method of claim 10, wherein the soft tissue is folded in a direction away from the suture anchor in the bone.

13. The method of claim 10, wherein attaching the first suture to the soft tissue includes wrapping the first suture around the soft tissue or stitching the first suture to the soft tissue.

14. The method of claim 10, wherein collapsing the collapsible suture includes cinching a knot of the collapsible suture.

15. The method of claim 10, wherein the soft tissue includes a biceps tendon.

16. A method for securing soft tissue to bone, comprising:
attaching first and second sutures to a portion of soft tissue to be attached or to be reattached to bone, the first and second sutures being spaced apart from one another and each having suture tails extending out of a patient's body;
inserting a suture anchor into bone, the suture anchor being inserted at a location proximal to an attachment site of the soft tissue, the suture anchor having a collapsible suture extending therefrom and extending out of the patient's body;
creating a folded segment of the soft tissue;
partially collapsing the collapsible suture such that the collapsible suture is within the folded segment adjacent to the suture anchor;
attaching the first and second sutures to each other by tying the suture tails together to trap the collapsible suture within the folded segment; and
tensioning the collapsible suture to approximate the segment to bone.

17. The method of claim 16, wherein the collapsible suture includes a collapsible suture loop; and
wherein the method further comprises:
passing one of the suture tails through the collapsible loop, and
passing the segment through the collapsible loop to create a folded segment.

18. The method of claim 16, wherein partially collapsing the collapsible suture includes cinching a knot of the collapsible suture.

19. The method of claim 16, wherein the soft tissue includes a biceps tendon.

* * * * *